United States Patent
Jez et al.

(10) Patent No.: US 7,795,582 B2
(45) Date of Patent: Sep. 14, 2010

(54) SYSTEM AND METHOD OF MONITORING WITH TEMPERATURE STABILIZATION

(75) Inventors: David R. Jez, Vancouver (CA); Frank M. Haran, Vancouver (CA)

(73) Assignee: Honeywell International Inc., Morristown, NJ (US)

( * ) Notice: Subject to any disclaimer, the term of this patent is extended or adjusted under 35 U.S.C. 154(b) by 37 days.

(21) Appl. No.: 11/875,415

(22) Filed: Oct. 19, 2007

(65) Prior Publication Data

US 2009/0101823 A1    Apr. 23, 2009

(51) Int. Cl.
- *G01J 11/00* (2006.01)
- *G01J 1/00* (2006.01)

(52) U.S. Cl. .................. 250/336.1; 250/338.1; 324/637; 324/639

(58) Field of Classification Search .............. 250/338.1, 250/341.1–347, 336.1; 324/637, 639
See application file for complete search history.

(56) References Cited

U.S. PATENT DOCUMENTS

| | | | |
|---|---|---|---|
| 4,013,260 A * | 3/1977 | McClatchie et al. ......... | 250/343 |
| 4,683,573 A | 7/1987 | Albanese | |
| 5,095,212 A | 3/1992 | Cook | |
| 5,181,214 A | 1/1993 | Berger et al. | |
| 5,729,017 A | 3/1998 | Brener et al. | |
| 5,789,750 A | 8/1998 | Nuss | |
| 5,894,125 A | 4/1999 | Brener et al. | |
| 5,914,497 A * | 6/1999 | Sherwin ...................... | 257/21 |
| 5,939,721 A | 8/1999 | Jacobsen et al. | |
| 6,078,047 A | 6/2000 | Mittleman et al. | |
| 6,388,799 B1 | 5/2002 | Arnone et al. | |
| 6,409,198 B1 * | 6/2002 | Weimer et al. ......... | 250/339.04 |
| 6,522,459 B1 | 2/2003 | Pease et al. | |
| 6,717,717 B2 | 4/2004 | Nelson | |
| 6,816,647 B1 * | 11/2004 | Rudd et al. ................... | 385/37 |
| 7,091,462 B2 | 8/2006 | Wilson et al. | |
| 7,244,934 B2 * | 7/2007 | Arnone et al. .......... | 250/336.1 |
| 2003/0011871 A1 | 1/2003 | Nelson | |
| 2003/0178584 A1 | 9/2003 | Arnone et al. | |
| 2004/0065832 A1 | 4/2004 | Cluff et al. | |
| 2004/0095147 A1 | 5/2004 | Cole | |
| 2005/0067579 A1 * | 3/2005 | Tsuchiya et al. ........ | 250/370.15 |

OTHER PUBLICATIONS

Tani et al. (1997). "Emission Characteristics of Photoconductive Antennas Based on Low-Temperature-Grown GaAs and Semi-Insulating GaAs." Applied Optics 36 (30): p. 7853-9.*

(Continued)

*Primary Examiner*—David P Porta
*Assistant Examiner*—Casey Bryant
(74) *Attorney, Agent, or Firm*—Jetter & Associates, P.A.

(57) ABSTRACT

A system and method of monitoring with temperature stabilization. The system can include a housing operably connected to a fiber optic cable that provides a light wave thereto, a relay optic for receiving the light wave and being positioned in the housing, a radiation device for processing or producing radiation in the frequency range of 10 GHz to 100 THz from the light wave and being positioned in the housing, a temperature sensor in thermal communication with the housing, and a thermal management device in thermal communication with the housing where the thermal management device adjusts a temperature within the housing based on temperature conditions measured by the temperature sensor. Other embodiments are disclosed.

20 Claims, 8 Drawing Sheets

OTHER PUBLICATIONS

Han, Pengyu and Zhang, Xi-Cheng. (2000) "Time-domain spectroscopy targets the far-infrared." Laser Focus World, vol. 45, Issue 10. Oct. 2000. [retrieved on Oct. 23, 2009 from <http://www.laserfocusworld.com/display_article/83863/12/none/none/Feat/Time-domain-spectroscopy-targets-the-far-infrared>].

Y. Cai, et al., Jul. 27, 1998, Coherent Terahertz Radiation Detection: Direct Comparison Between Free-Space Electro-Optic Sampling and Antenna Detection, Applied Physics Letters, vol. 73, No. 4.

G. Zhao, et al., Apr. 2002, Design and Performance of a THz Emission and Detection Setup Based on a Semi-Insulating GaAs Emitter, Review of Scientific Instruments, vol. 73, No. 4.

* cited by examiner

SYSTEM AND METHOD OF MONITORING WITH TEMPERATURE STABILIZATION

FIELD OF THE INVENTION

This disclosure relates generally to control systems and more specifically to a system and method of monitoring with temperature stabilization.

BACKGROUND

Processing facilities, such as manufacturing plants, chemical plants and oil refineries, are typically managed using process control systems. Valves, pumps, motors, heating/cooling devices, and other industrial equipment typically perform actions needed to process materials in the processing facilities. Among other functions, the process control systems often manage the use of the industrial equipment in the processing facilities.

In conventional process control systems, controllers are often used to control the operation of the industrial equipment in the processing facilities. The controllers can typically monitor the operation of the industrial equipment and/or the products or related materials through use of various sensors, and provide control signals to the industrial equipment based on information retrieved from the various sensors. However, control steps are often highly dependent upon measured or otherwise sensed data from the sensors, and inaccuracies or delays in receipt of the data can have a significant effect on the control process.

One such sensor that can be used in a control process utilizes terahertz electromagnetic radiation, such as generated by a pulsed laser. The laser can be pointed directly through space, including at an optical switching element, with negligible dispersive effects. There are drawbacks with the use of a free-space laser pulse, such as being deflected by objects or people and suffering degradation from atmospheric effects or other environmental conditions. Additionally, frequent realignment may be required due to environmental effects, such as on the material properties of the alignment mechanisms.

Industrial and other environments can pose other problems for a terahertz monitoring system. The presence of temperature fluctuations, vibration and atmospheric effects (e.g., humidity and/or air turbulence) can adversely influence the ability to obtain accurate and repeatable measurements. Temperature fluctuations can induce drift in the terahertz transceivers, which adversely effect the measurement.

Accordingly, there is a need for a method and system for monitoring with temperature stabilization. There is a further need for such a method and system that facilitates use of the monitoring system, such as positioning in difficult to reach locations.

SUMMARY

The Summary is provided to comply with 37 C.F.R. §1.73, requiring a summary of the invention briefly indicating the nature and substance of the invention. It is submitted with the understanding that it will not be used to interpret or limit the scope or meaning of the claims.

In one exemplary embodiment of the present disclosure, a method of temperature stabilized sensing of processing parameters can include coupling electromagnetic waves into at least one housing where the housing has a radiation generator system and a radiation detector therein and where the radiation generator system receives the electromagnetic waves and provides output radiation in a frequency range from 10 GHz to 100 THz, directing the output radiation towards a sample in a processing system, sensing temperature conditions associated with the housing while receiving radiation emanating from the sample where a temperature within the housing is controlled based on the sensed temperature conditions using a thermal management device thermally coupled to the housing.

In another exemplary embodiment, a device for monitoring a sample or or process is provided. The device can include a housing operably connected to a fiber optic cable that provides a light wave thereto, a relay optic for receiving the light wave and being positioned in the housing, a radiation device for processing or producing radiation in the frequency range of 10 GHz to 100 THz from the light wave and being positioned in the housing, a temperature sensor in thermal communication with the housing, and a thermal management device in thermal communication with the housing. The thermal management device can adjust a temperature within the housing based on temperature conditions measured by the temperature sensor.

In a further exemplary embodiment, a system for monitoring a sample or process is provided. The system can include a laser for generating a light wave, a transmitter coupled to the laser by a fiber optic cable for receiving the light wave where the transmitter produces radiation in the frequency range of 10 GHz to 100 THz and where the transmitter applies the radiation to the sample or process, a receiver for receiving and processing the radiation applied to the sample or process, and an air purging device in fluid communication with the sample or process. The air purging device can apply an inert gas to a path of the radiation in proximity to the sample or process.

The technical effect includes, but is not limited to, allowing for accurate and repeatable measurements by way of imaging or spectroscopy. The technical effect further includes, but is not limited to, stabilizing the temperature in and around the measuring devices to allow for the accurate and repeatable measurements.

The above-described and other features and advantages of the present disclosure will be appreciated and understood by those skilled in the art from the following detailed description, drawings, and appended claims.

DETAILED DESCRIPTION OF THE INVENTION

Figure 1:
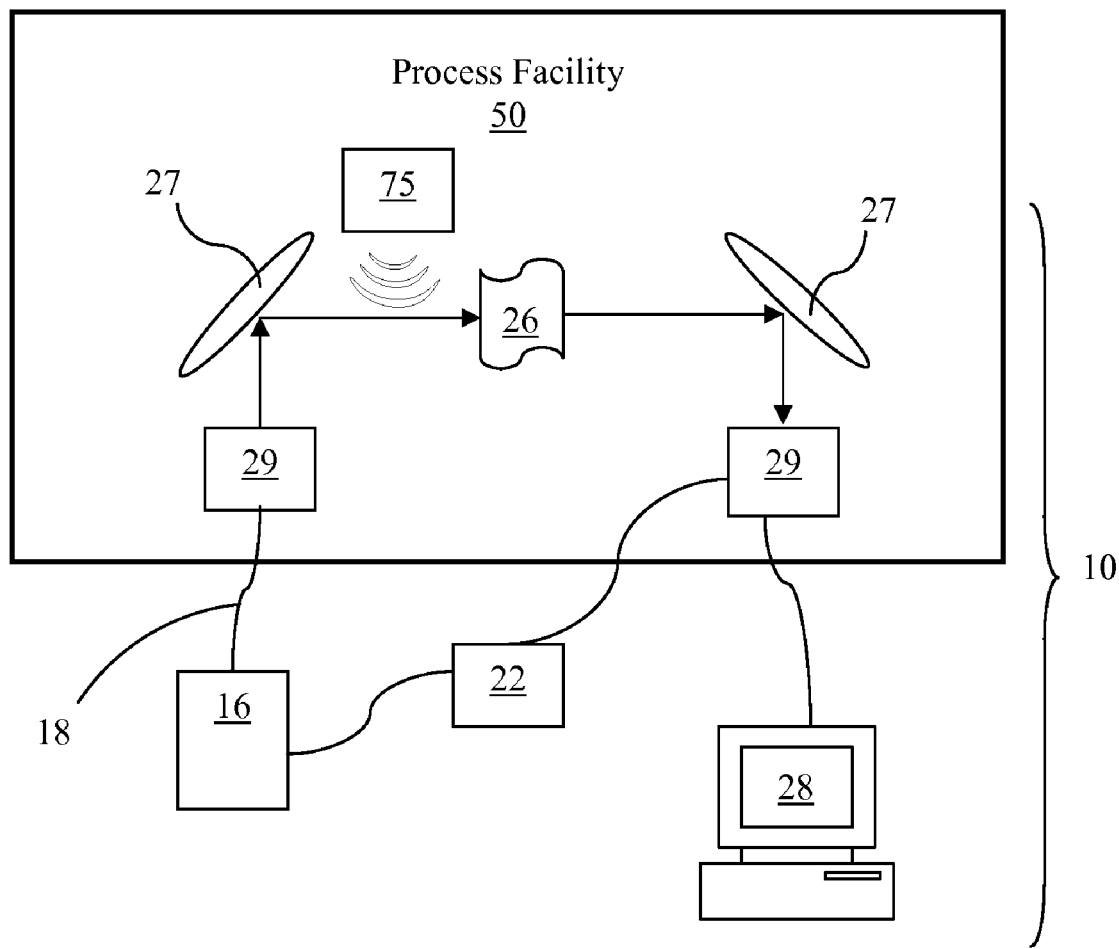
FIG. 1 is a schematic illustration of an exemplary monitoring system using terahertz radiation according to an embodiment of the present invention.

Referring to the drawings, and in particular to FIG. 1, a monitoring system in accordance with one exemplary embodiment of the invention is shown and is generally represented by reference numeral 10. Monitoring system 10 can be used with various processing facilities, various processes and/or various samples, including manufacturing processes, chemical plants, oil refineries and paper products. The particular type of facility or process and/or the particular type of sample that is to be monitored or measured is not intended to be limited.

Monitoring system 10 can be in communication with, coupled to, or part of, a control system (not shown) that can provide for control of a process, including a multi-variable process. In one embodiment, the monitoring system 10 can obtain data associated with a non-linear process, but the present disclosure also contemplates the use of the monitoring system 10 for measuring or otherwise sensing aspects in linear processes.

Monitoring system 10 can generate and detect electromagnetic waves, such as terahertz (THz) waves, for monitoring various properties of a process or a sample. The system 10 can include a pulsed laser 16, such as a Ti:sapphire laser. The present disclosure contemplates the use of other lasers, including a Cr:LiSAF laser, a Cr:LiSGAF laser, a Cr:LiSCAF laser, an Er-doped Fiber laser, an Yb-doped fiber laser and gain switched diode lasers, as well as the use of continuous wave sources, such as gallium arsenide photomixers. The pulsed laser can be incident on a photoconductive antenna or an optical rectification crystal, such as ZnTe.

The laser 16 can be coupled by a fiber optic cable 18 or other optical conduit to a first THz transceiver 29 via an optical delay 22 and to a second THz transceiver 29. The present disclosure describes the use of THz transceivers 29, although the present disclosure contemplates the use of transceivers that can receive and/or transmit electromagnetic waves along any portion of the spectrum. Optical system 27 is also shown with the monitoring system 10. The first transceiver 29 can be used as a transmitter of the THz radiation, while the second transceiver 29 can be used as a receiver of the radiation. While the present disclosure describes the first and second transceivers 29 as being capable of both transmitting and receiving, it should be understood by one of ordinary skill in the art that the devices can instead be separate, dedicated devices that each perform only one of the transmitting and receiving.

The THz transmitter 29 can generate THz radiation that propagates through the first optical system 27, through a sample 26 of the processing facility 50, through the second optical system 27, and then is received by the THz receiver 29. The THz receiver 29 can output a signal representative of the received THz radiation. The optical delay 22 can determine which temporal portion of the signal is gated by the pulse at the THz receiver 29. In one embodiment, the optical delay 22 can be controlled by a controller 28 (e.g., a desktop computer) that can also receive the output signal of the THz receiver 29. The optical system 27 can be of various types, including a collimating optical element.

System 10 allows for positioning of the transceivers 29 in remote or difficult to reach places, such as in a paper mill, while other components of the system, such as the laser 16, controller 28 and lock-in amplifiers, are easily accessible, for example to facilitate maintenance of the system. The use of the fiber optic cable 18 allows the radiation generated by laser 16 to propagate along the cable without being measurably affected by atmospheric conditions (e.g., temperature fluctuations in the facility) or alignment drift.

Figure 2:
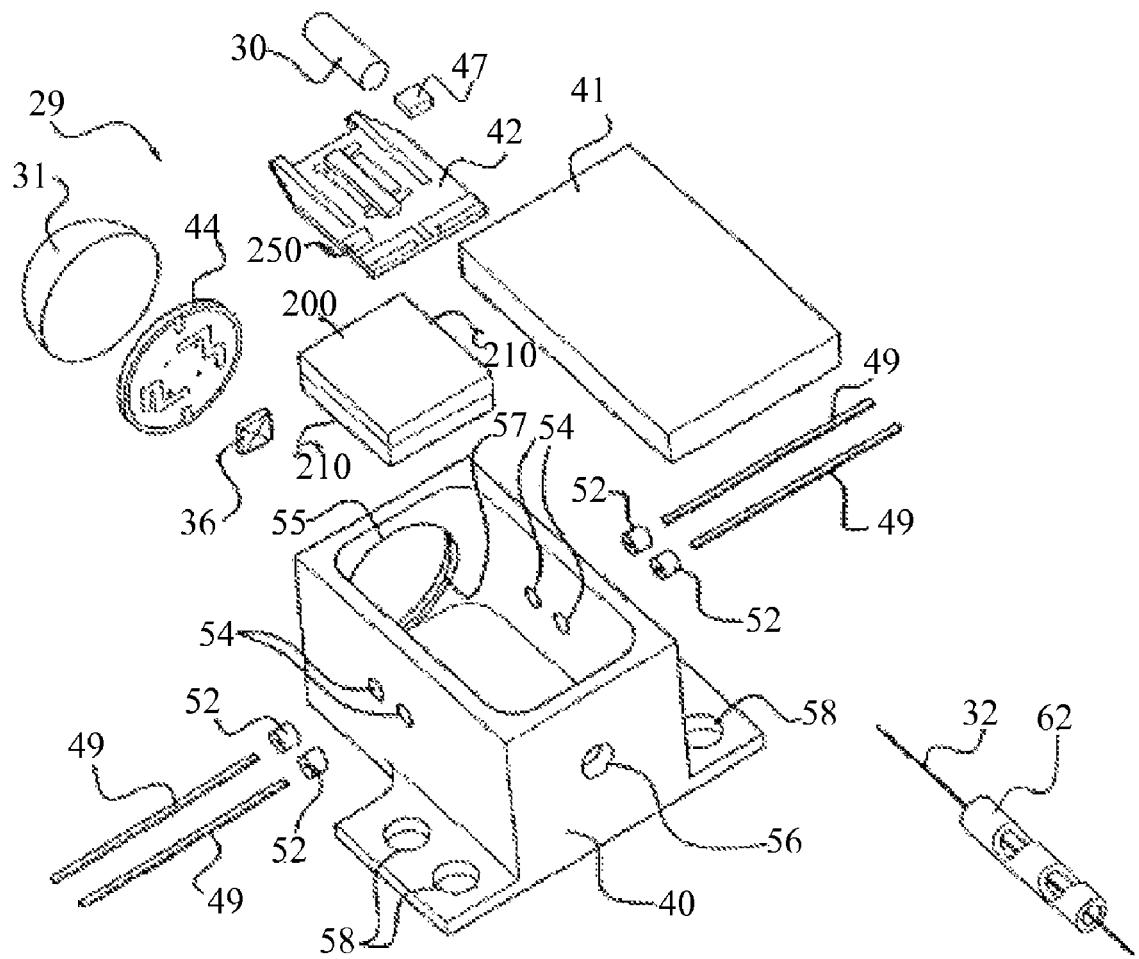
FIG. 2 is an exploded perspective view of a terahertz transceiver of the system of FIG. 1.
Figure 3:
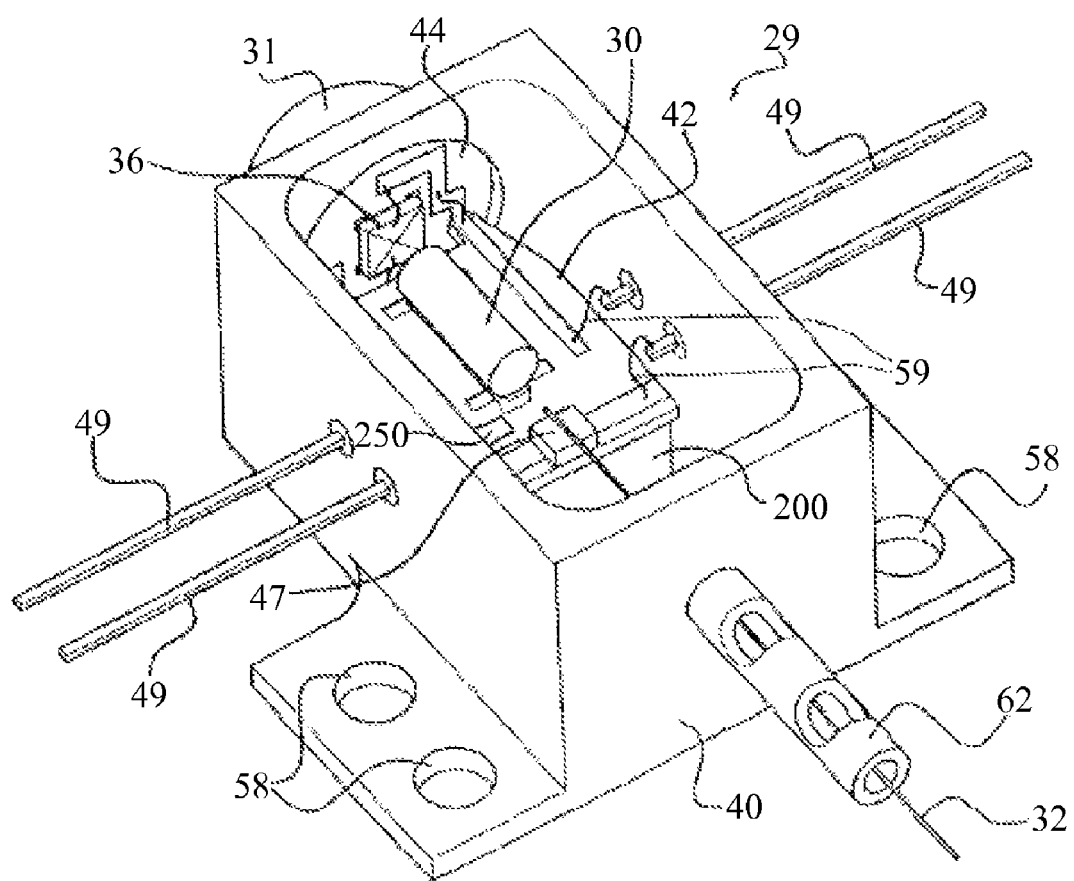
FIG. 3 is a perspective view of the terahertz transceiver of the system of FIG. 1.
Figure 4:
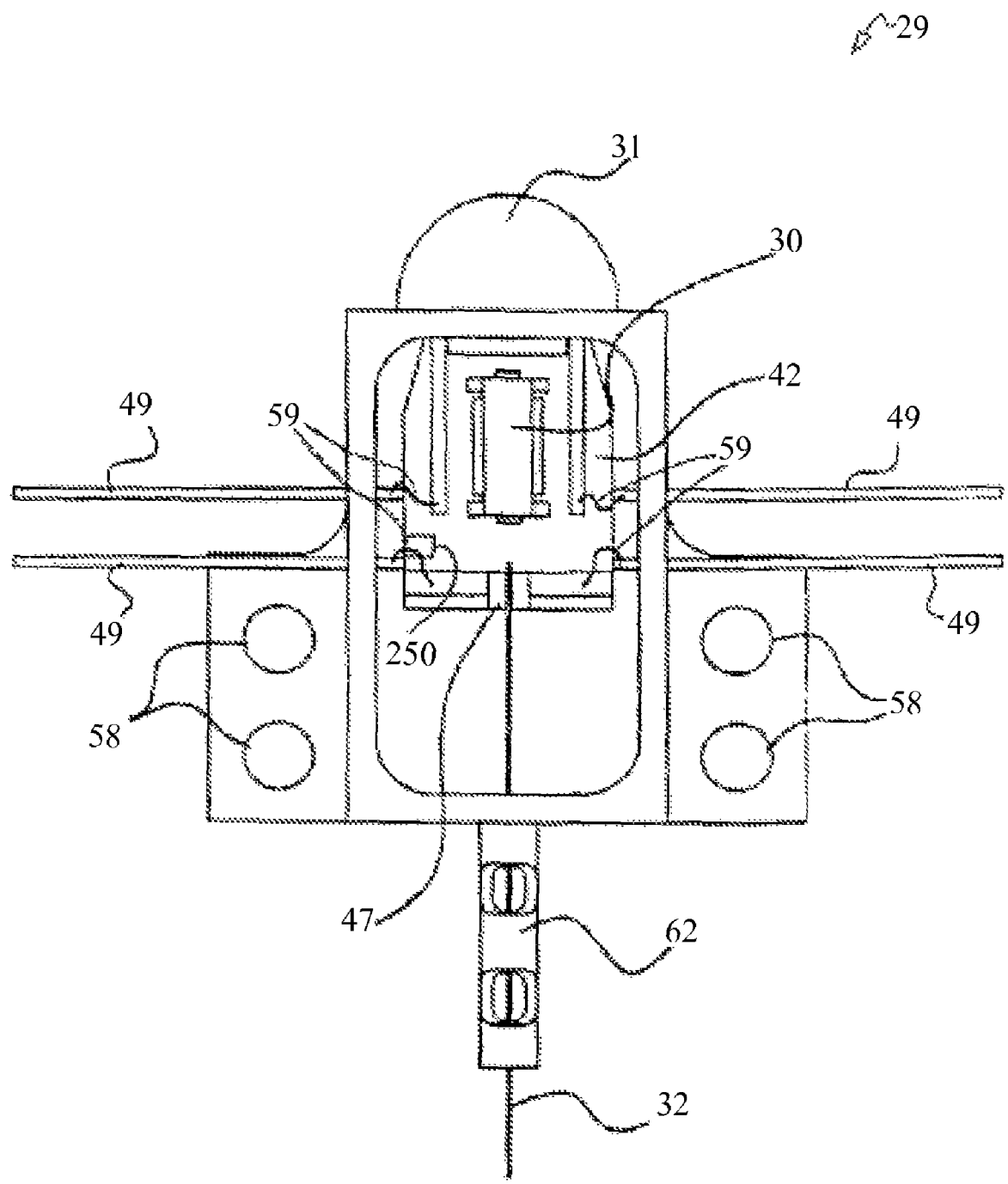
FIG. 4 is a plan view of the terahertz transceiver of the system of FIG. 1.

Referring additionally to FIGS. 2 through 4, components of the THz transceivers 29 are more clearly shown. The transceiver 29 can have a radiation generating system or device, such as a terahertz device 36, mounted within the transceiver for generating and/or detecting the electromagnetic radiation. The terahertz device 36 can have a pair of electrodes bonded to a semiconductor substrate, such as a low-temperature-grown gallium arsenide substrate. Transceiver 29 can also include a relay optic 30 (e.g., a gradient index lens), which can focus the output of optical fiber 32 down to the optimal spot size and/or remove the fiber 32 from the immediate vicinity of the terahertz device 36.

The transceiver can also include a housing 40, such as an industrial hardened case, with a lid 41 that seals the transceiver components to protect them from environmental variables and rough handling. In one embodiment, the housing 40 can be hermetically sealed. In another embodiment, the housing 40 can contain a dry inert gas, such as nitrogen. A plurality of electrical conductor pins 49 can be bonded to electrically insulating bushings 52 which are pressed into and bonded to bushing apertures 54 in the housing 40. A fiber aperture 56 can be disposed in the housing 40 and configured to receive a ferrule 62 having fiber 32 bonded thereto. A plurality of mounting apertures 58 can be provided in housing 40 to mechanically secure the transceiver 29 to a mounting surface. Housing 40 can have various shapes and sizes, including conforming to standard shapes of parts, such as dual in-line or small outline plastic packages.

Transceiver 29 can also include an optic mounting plate or substrate 42 and a window 44. The plate 42 can support or otherwise hold the optical relay 30, fiber pillow block 47, fiber 32 and/or terahertz device 36 in place, as well as providing electrical contacts for the device. The plate 42 can be made from various materials, including alumina. In one embodiment, the terahertz device 36, the optical relay 30 and the fiber 32 are all connected to the plate 42 to reduce misalignment between these components, such as could occur due to vibration. In another embodiment, a window 44 can be provided for ease of assembly of the terahertz device 36 to the housing 40. Window 44 can be silicon or other compatible material, and can be soldered, bonded or otherwise connected to the housing 40, such as along surface 57 defining a window aperture 55. A terahertz lens 31 can be mounted onto the window 44 for reducing the divergence of the electromagnetic wave radiation emanating from the terahertz device 36. The lens 31 can be silicon, sapphire, alumina, or another type, and the configuration of the lens 31 can be generally aplanatic.

The transceiver 29 can include a fiber pillow block 47 to position the fiber 32 at the appropriate height above a bottom inside surface of the housing 40 to ensure optical fiber alignment with the relay optic 30 and the terahertz device 36. In one embodiment, the fiber pillow 47 can be integrally formed with the plate 42. However, the present disclosure also contemplates the fiber pillow block 47 being bonded to the mounting plate 42 using solder or epoxy, or other connecting structure or techniques being utilized. This can allow the fiber 32 to be manipulated until the THz signal is optimized. Solder or epoxy can then be deposited onto the fiber pillow block 47 to encase the fiber 32. Other materials, such as thermal grease or padding can be used to facilitate heat transfer from the fiber 32 through the block 47 and plate 42. The fiber 32 can be mounted remotely from relay optic 30. Electrical jumpers 59 can be used for connection between the plate 42 and the pins 49.

The present disclosure also contemplates the fiber 32 being integrated with the relay optic 30 to create a fiber assembly, such as through bonding the fiber to the relay optic using solder, epoxy or other appropriate bonding agent. Alignment of the fiber assembly can then be achieved by actively manipulating the entire assembly, not just the fiber. In another embodiment (not shown), the relay optic 30 can be integrated into the optical fiber 32, such as by forming the relay optic out of the optical fiber material and configuring it to create a de-magnifying lens which would serve the same function as the relay optic.

To provide for thermal management of the THz transceiver 29, a thermal management device 200 can be provided. For example, the thermal management device 200 can be a thermo-electric device or cooler that can cool targeted components of the transceiver, such as the optic relay 30, the fiber 32 and/or the terahertz device 36. In another embodiment, the device 200 can cool the inner volume of the housing 40 to compensate for heat being generated, such as by the electrical components, and/or heat in the facility 50. The present disclosure also contemplates the thermal management device 200 being able to heat various components and/or heat the inner volume of the housing 40, such as through reversing the current flow to the thermo-electric device (e.g., a reversible Peltier device). In another embodiment, the heating/cooling device 200, which is capable of quickly alternating between heating and cooling of a particular element, can be a thermionic device. Thermionic refrigeration is described by G. D. Manhan and L. M. Woods, "Multilayer Thermionic Refrigeration," in *Physical Review* Letters, Vol. 80, Number 18 4016-4019 (The American Physical Society 1998) and is incorporated by reference herein. Cooling is obtained in thermionic emission after thermally excited electrons escape over a barrier, with the barrier typically being a semiconductor. Such a device can have an expected efficiency somewhere between one and two, which is similar to Freon-based refrigeration.

The thermo-electric cooler 200 can be provided with power and/or control signals through lines 210. A sensor 250, such as a temperature transducer and/or humidity detector, can be used for detecting conditions within the housing 40. In one embodiment, the sensor 250 can be coupled to the controller 28, such as through a wireline and/or wireless link, to provide the controller with data regarding the THz transceiver conditions, including the temperature of various components of the transceiver and/or the temperature within housing 40. The controller 28 can provide control signals and/or regulate the power provided to the thermo-electric cooler 200 in order to control the temperature or other conditions in the housing 40. In another embodiment, the thermoelectric cooler 200 can have its own controller (not shown) that is connected directly to the temperature sensor 250 and that controls the temperature in the housing 40, such as through current regulation. In yet another embodiment, the thermo-electric cooler 200 can utilize power provided to the other components of the transceiver 29, such as by conductor pins 49 and jumpers 57.

In the exemplary embodiment of FIGS. 1-4, the thermo-electric cooler 200 can be in direct and thermal contact with the plate 42 upon which the components to be temperature stabilized sit. One or more of the optic relay 30, the fiber 32 and the terahertz device 36 can be directly connected to the plate 42 which is in direct contact with the thermo-electric device 200. In another embodiment, the thermo-electric cooler 200 can be positioned through an opening formed in the housing 40 and secured therein by various structure and techniques, including soldering or bonding.

The particular size, number, configuration and thermal management capacity of the thermo-electric cooler 200 can vary depending on a number of factors, including the expected thermal load of the transceiver components. For instance, the exemplary embodiment of FIGS. 2-4 shows a single thermo-electric cooler 200 positioned under the plate 42 where the cold side is contained within the housing 40. The hot side of the thermo-electric cooler 200 can be positioned outside of the housing 40 and/or in thermal contact with the outside of the housing. In another exemplary embodiment, the hot side of the thermo-electric cooler 200 can be flush with a wall of the housing 40. heat sinks can be positioned in direct and/or thermal contact with the thermo-electric cooler 200 to facilitate heat transfer with respect to the plate 42 and/or the targeted components, such as the optic relay 30, the fiber 32 and the terahertz device 36. This configuration can reduce or minimize thermal gradient between these components and can reduce or minimize the thermal response time of the control loop. The temperature sensor 250 in the closed loop can be directly and/or thermally contacted to the plate.

Figure 5:
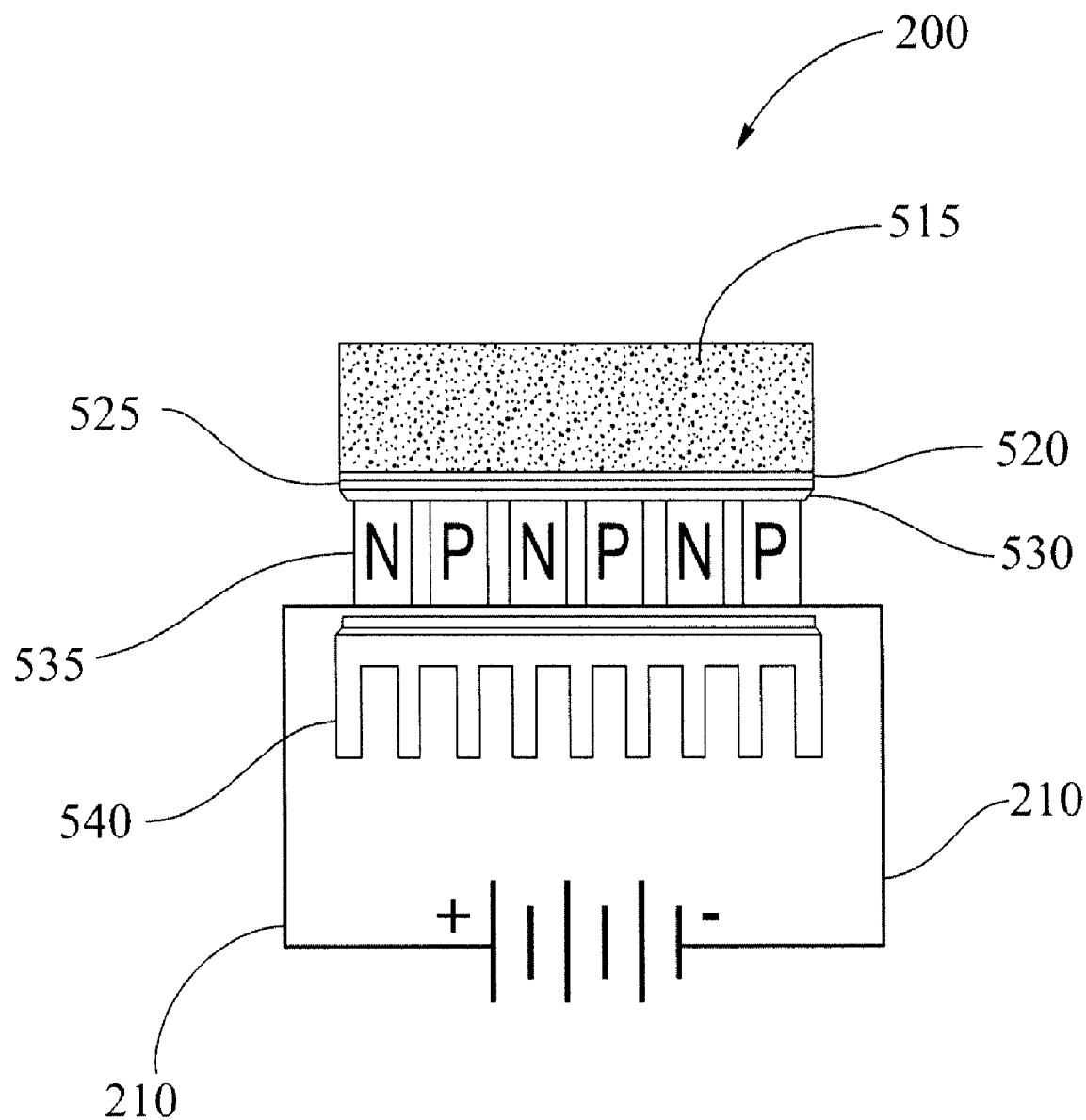
FIG. 5 is a schematic illustration of a thermo-electric device of the terahertz transceiver of FIG. 2.

Referring additionally to FIG. 5, the thermo-electric cooler 200 can have a heat sink or other thermally conductive material 515 along the cold side, one or more N-doped semi-conductors 535 and one or more P-doped semi-conductors 535 in series with each other, and a heat sink or other thermally conductive material 540 along the hot side. The N-doped and P-doped materials 535 can vary, including bismuth telluride pellets. The heat sinks 515 and 540 can be respectively separated from the N-doped and P-doped materials 535 through one or more of a thermal interface material 520 (e.g., thermal grease, thermal pad, thermal putty or solder), a ceramic plate 525 to act as both a thermal conductor and an electrical insulator, and copper traces 530 that can connect each of the N-doped and P-doped materials in series. A current can be applied to the N-doped and P-doped materials 535, such as through the lines 210 connected to a power source or supply. The particular size, shape and material for each of the heat sinks 515 and 540 can vary, including aluminum heat fins.

Figure 6:
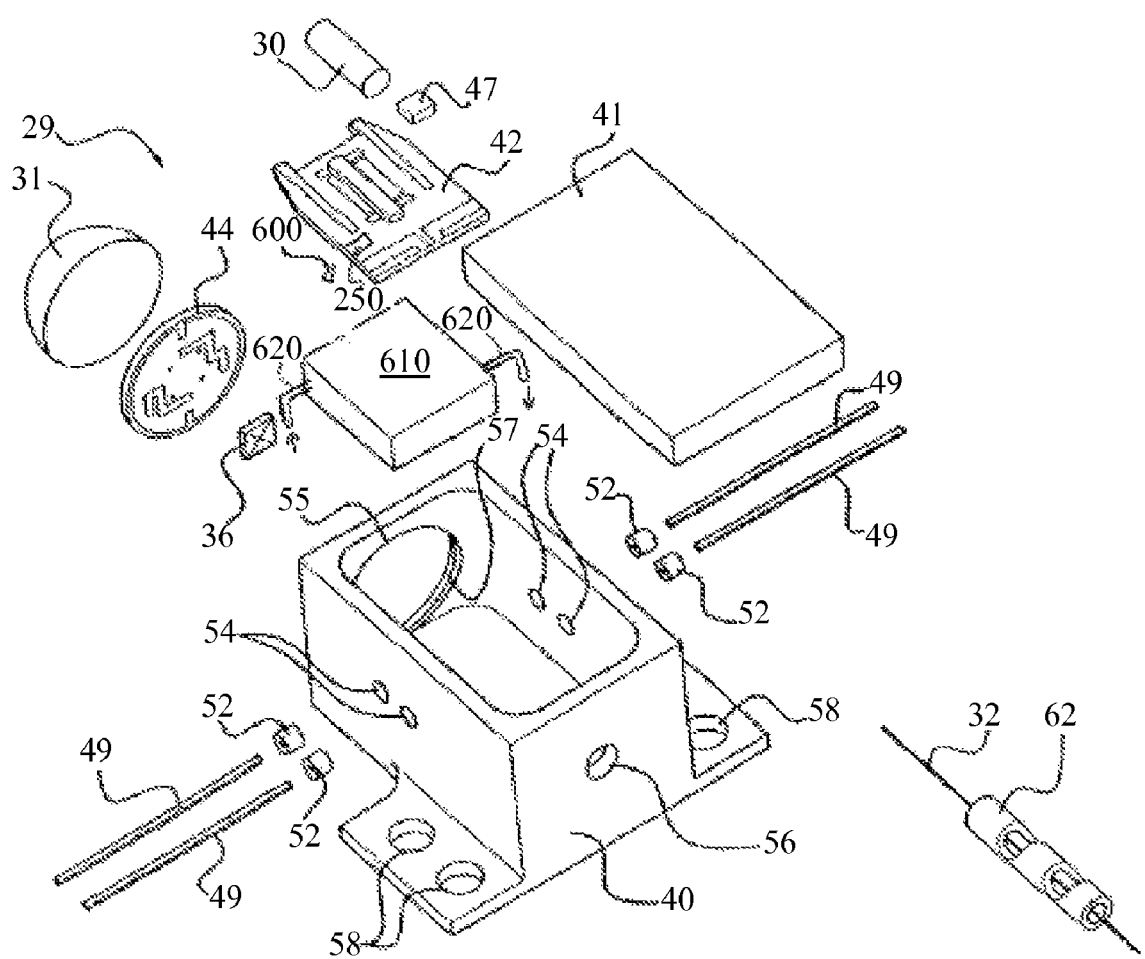
FIG. 6 is an exploded perspective view of another exemplary terahertz transceiver of the system of FIG. 1.

Referring to FIG. 6, where similar features are labeled by the same reference numerals as in FIGS. 2-4, the transceiver 29 is shown using a fluid thermal management device 600. Similar to the device 200 described above, data from the sensor 250 can be used for regulating the cooling and/or heating of one or more of the optic relay 30, the fiber 32 and the terahertz device 36, and/or for regulating the temperature of the inner volume of housing 40 by the fluid thermal management device 600. The device 600 can include one or more heat sinks 610 in the housing 40. The heat sinks 610 can have various sizes and shapes depending on a number of factors including the thermal load to be managed and the size and shape of the housing 40. The heat sink 610 can be in fluid communication with a cooling fluid for removal of heat therefrom, such as through use of conduits 620 that can pass through openings in the housing 40. The conduits 620 can be part of a cooling circuit with various components, such as a vapor-compression circuit, although other cooling circuits are contemplated, including forced air convection, forced fluid convection and/or natural convection.

In one embodiment, the fluid thermal management device 600 can utilize a thermal or heat pipe, such as for the conduits 620. The thermal pipe 620 can be a sealed hollow tube made of a thermoconductive metal, such as copper or aluminium, that contains a working fluid (e.g., water, ethanol or mercury) with the remainder of the tube being filled with vapour phase of the working fluid. On the internal side of the tube's sidewalls, a wick structure can exert a capillary force on the liquid phase of the working fluid. The wick structure can be any material or structure capable of soaking up the working fluid, such as a sintered metal powder or a series of grooves parallel to the tube axis. The amount of working fluid can be regulated to control the amount of cooling or heating.

Figure 7:
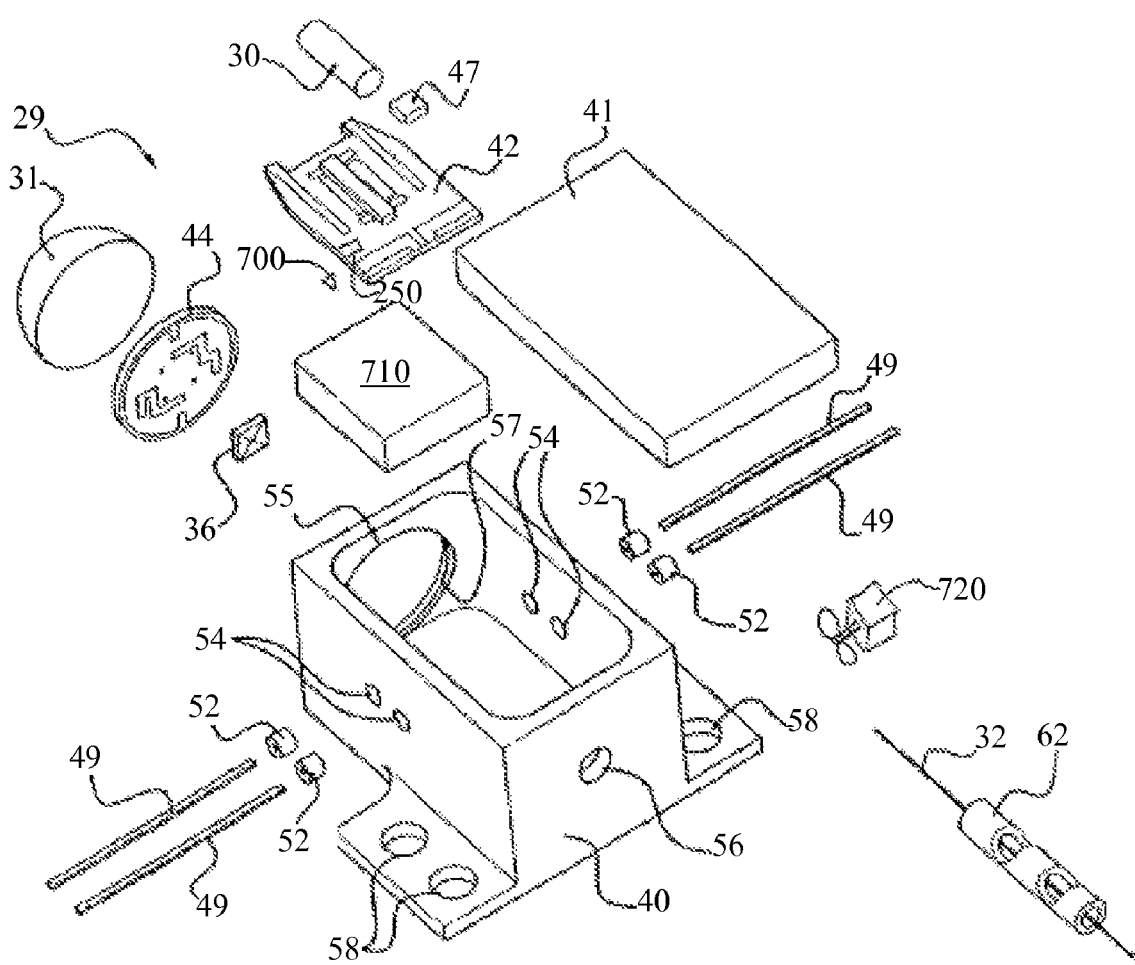
FIG. 7 is an exploded perspective view of another exemplary terahertz transceiver of the system of FIG. 1.

Referring to FIG. 7, where similar features are labeled by the same reference numerals as in FIGS. 2-4, the transceiver 29 is shown using a forced air thermal management device 700. Similar to the device 200 described above, data from a sensor 250 can be used for regulating the cooling and/or heating of one or more of the optic relay 30, the fiber 32 and the terahertz device 36, and/or for regulating the temperature of the inner volume of housing 40 by the device 700. The device 700 can include one or more heat sinks 710 that are in direct and/or thermal contact with the plate 42. The heat sink 710 can be partially disposed in the housing 40 and partially disposed outside of the housing. The heat sink 710 can have various sizes and shapes depending on a number of factors including the thermal load to be managed and the size and shape of the housing 40. For example, the heat sink 710 can be a single structure being shaped as a plate and positioned under the plate 42. In another embodiment, the heat sink 710 can be a ring with the fiber 32 and/or optic relay 30 positioned through the opening in the ring. The heat sink 710 can be in fluid communication with one or more fans 720 for removal of heat therefrom using forced air convection. The number, size and configuration of the one or more fans 720 can vary depending on a number of factors including the thermal load to be managed and the size and shape of the housing 40.

In one embodiment, the fan 720 can be a variable frequency drive (VFD) fan that allows for control of the rotational speed of an alternating current electric motor rotating the fan blades by controlling the frequency of the electrical power supplied to the motor. The VFD fan 720 can allow the fan speed to be continuously adjusted, such as by the controller 28, in response to data provided by the sensor 250 in the housing 40.

Figure 8:
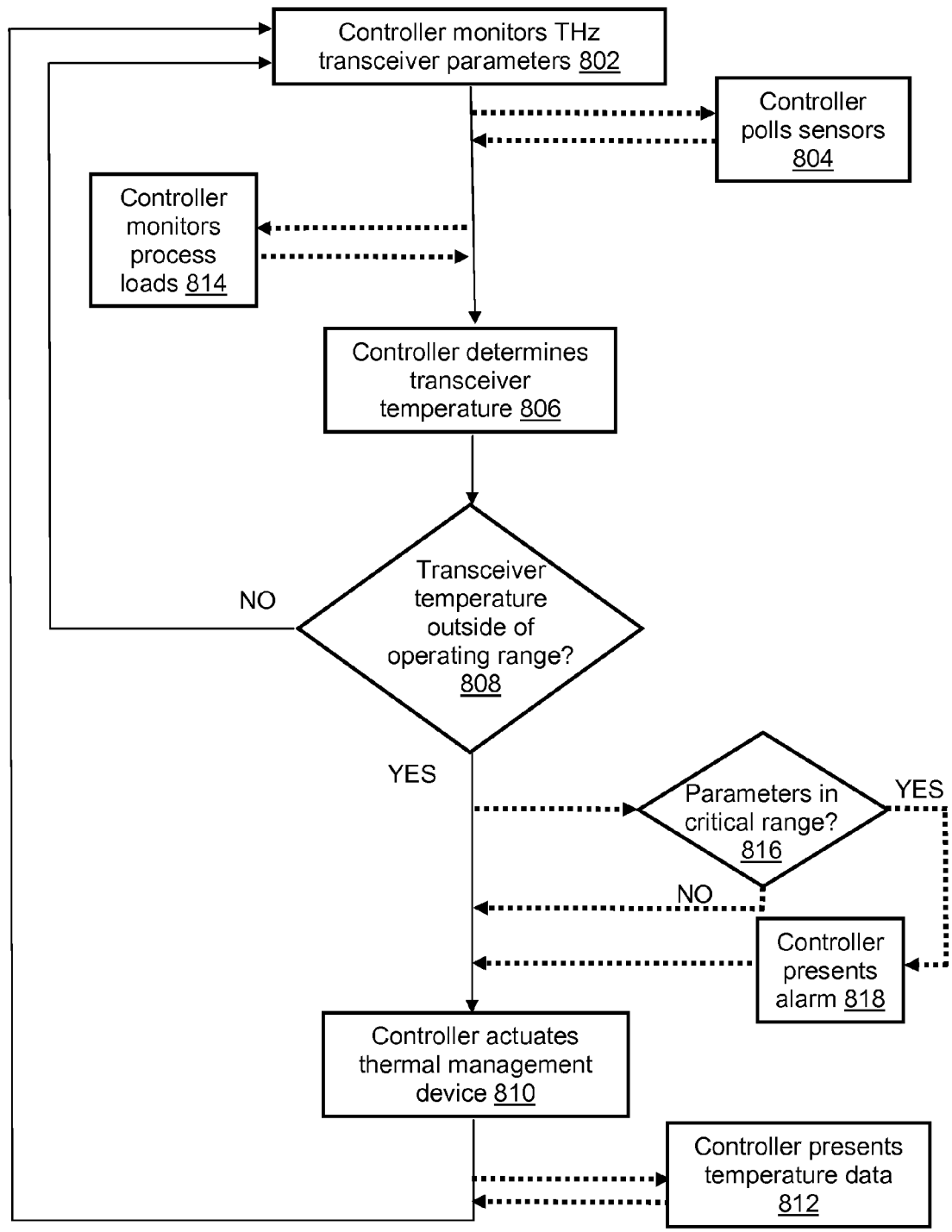
FIG. 8 is a flow chart illustrating an exemplary method for temperature stabilization of the terahertz transceivers according to an embodiment of the present invention using the system and/or devices of FIGS. 1 through 7.

FIG. 8 depicts an exemplary method 800 operating in portions of the monitoring system 10. Method 800 has variants as depicted by the dashed lines. It would be apparent to an artisan with ordinary skill in the art that other embodiments not depicted in FIG. 8 are possible without departing from the scope of the claims described below. Method 800 is described with reference to thermal management device 200, but the present disclosure contemplates the use of any of the thermal management devices described herein or otherwise usable with system 10 for stabilizing the temperature of the THz transceiver 29.

Method 800 begins with step 802 in which the controller 28 can monitor for parameters or conditions of the THz transceivers 29. The conditions can vary and can come from a variety of sources, including the temperature sensor 250 in the housing 40 of transceiver 29. In one embodiment, the controller receiving the data can be incorporated with the transceiver 29, such as in the housing 40, to provide for autonomous control of thermal management of the transceiver.

In another embodiment in step 804, the controller 28 or other processor can poll the sensor 250, such as sending a polling signal to each of the sensors at a fixed or adjustable interval to retrieve the corresponding data. In another embodiment, the sensors 250 can provide the corresponding data at scheduled intervals. The particular length of the interval and whether it is adjustable can vary. For instance, a shortened data retrieving interval may be used for a thermal load of the transceiver that fluctuates frequently.

In step 806, the controller 28 can determine the temperature in or associated with the housing 40 and/or the temperature of one or more components of the transceiver. In step 808, the controller 28 can determine whether the transceiver current operating temperature is outside of a target range. If the current operating temperature is not outside of the target range then method 800 can return to step 802 to continue monitoring the parameters or conditions of the THz transceivers 29. If on the other hand, the current operating temperature is outside of the target range then in step 810 the controller 28 can actuate or otherwise adjust the thermal management device 200, and return to monitoring of the system parameters. The determination of whether the current operating temperature of the transceivers 29 is outside of the target range, as opposed to determining if the current operating temperature is different from a target temperature, can include determining whether the current operating temperature is within the deadband factor which could induce limit cycling.

In one embodiment in step 812, the controller 28 can present the data (e.g., temperature in the housing 40) or a portion of the data. For example, the data can be presented in real-time. The data can be presented in various forms, such as graphs and the like, and can be manipulated data including providing historical information associated with the data. As another example, particular time periods that have had historically higher housing temperatures or thermal loads can be presented to a technician in combination with presenting the current housing temperature or thermal load.

In another embodiment in step 814, the controller 28 can monitor for process loads or activities of the process. The process loads or activities can be used to predict changes to the temperature associated with the housing 40. This information can be used for adjusting the thermal management device 200. For example, the controller 28 can monitor for a drying step in a paper making process where heat is generated in the facility 50 that can raise the temperature in and around the transceivers 29.

In another embodiment in step 816, the controller 28 can determine whether the housing temperature is in a critical range. If the housing temperature is not in a critical range then the controller 28 can present the data in a typical fashion (e.g., at a display monitor of a user interface), but if the parameters are in a critical range then in step 818 the controller 28 can present an alarm to a technician.

Monitoring system 10 can provide a temperature stabilized measuring and/or sensing system that can be used with various samples and/or processes. The monitoring system 10 can provide for real-time temperature stabilization of transceivers 29 of the system 10 to avoid inaccuracies in the measurements, such as through temperature fluctuations. While the exemplary embodiments are described with respect to radiation in the range of 10 GHz to 100 THz, the present disclosure contemplates use of other spectrums of electromagnetic radiation for monitoring. Additionally, the exemplary embodiments of thermal management devices 200, 600 and 700 can be used alone or in combination with each other. The present disclosure also contemplates the use of other thermal management devices and techniques to be used for temperature stabilization of the transceivers 29.

The monitoring system 10 also contemplates improving monitoring through the use of other components and techniques to be used alone or in combination with the thermal management devices 200, 600 and 700, including air purging of the THz beam path from the transceiver 29 to the sample 26. Air purging can control or alleviate the effect of humidity and/or air turbulence. Various devices and techniques can be used, including exposing the sample 26 to an inert gas, such as nitrogen, from an air purging device 75 (FIG. 1). For example, in a paper making process there can be high humidity levels that can effect monitoring through use of terahertz radiation. System 10 allows for accurate monitoring despite the high humidity levels by lowering and stabilizing the humidity in the THz beam path between the sensor head and the paper sheet.

The present disclosure also contemplates the use of a computer system within which a set of instructions, when executed, may cause the machine to perform any one or more of the methodologies discussed above. The computer instructions can be embodied in a storage medium. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, the term "machine" shall be taken to include a single machine or any collection of machines that individually or jointly execute a set (or multiple sets) of instructions to perform any one or more of the methodologies discussed herein.

The computer-readable storage medium can have stored thereon one or more sets of instructions (e.g., software) embodying any one or more of the methodologies or functions described herein, including those methods illustrated above. The computer-readable storage medium can be an electromechanical medium such as a common disk drive, or a mass storage medium with no moving parts such as Flash or like non-volatile memories. The instructions may also reside, completely or at least partially, within a main memory, a static memory, and/or within a processor during execution thereof by the computer system. The main memory and the processor also may constitute computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein. The present disclosure contemplates a machine readable medium containing instructions, or that which receives and executes instructions from a propagated signal so that a device, such as connected to a network environment can send or receive data, and to communicate over the network using the instructions.

While the computer-readable storage medium can be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a computer-readable storage medium or a distribution medium, as listed herein and including art-recognized equivalents and successor media, in which the software implementations herein are stored.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

What is claimed is:

1. A method of temperature stabilized sensing of processing parameters, the method comprising:

coupling electromagnetic waves into at least one housing, said housing having a radiation generator system and a radiation detector therein, wherein said radiation generator system receives said electromagnetic waves and provides output radiation in a frequency range from 10 GHz to 100 THz;

directing said output radiation towards a sample in a processing system; and sensing temperature conditions associated with the housing while receiving radiation emanating from said sample and a time gating pulse at said radiation detector for providing a time gated detector output, wherein a temperature within the housing is controlled based on the sensed temperature conditions using a thermal management device thermally coupled to the housing.

2. The method of claim 1, further comprising providing a fiber optic cable to deliver said electromagnetic waves into said housing.

3. The method of claim 2, wherein the thermal management device is a thermo-electric device, and wherein the temperature conditions associated with the housing include a temperature of at least one of the relay optic, the radiation generating system and the fiber optic cable.

4. The method of claim 2, further comprising the step of gas purging a path of the radiation in proximity to the sample being monitored.

5. The method of claim 1, wherein the adjusting of the temperature within the housing is by at least one of forced fluid convection and forced air convection.

6. The method of claim 1, further comprising the step of presenting information associated with at least one of the sensed temperature conditions associated with the housing and the adjusting of the temperature within the housing.

7. A device for monitoring a sample, the device comprising:

a housing operably connected to a fiber optic cable that provides a light wave thereto;

a relay optic for receiving the light wave and being positioned in the housing;

a radiation generating device for generating output radiation in the frequency range of 10 GHz to 100 THz from the light wave and being positioned in the housing;

an optical system for directing said output radiation to said sample;

a radiation detector in the housing for receiving radiation emanating from said sample and a time gating pulse for providing a time gated detector output;

a temperature sensor in thermal communication with the housing; and a thermal management device in thermal communication with the housing, wherein the thermal management device adjusts a temperature within the housing based on temperature conditions measured by the temperature sensor.

8. The device of claim 7, wherein the thermal management device is a thermo-electric device, wherein at least one of the relay optic, the radiation device and the fiber optic cable are mounted to a mounting plate, wherein the thermo-electric device is in thermal communication with the mounting plate, and wherein the temperature conditions associated with the housing include a temperature of the mounting plate.

9. The device of claim 8, wherein the thermo-electric device has a first portion disposed inside of the housing and a second portion disposed outside of the housing.

10. The device of claim 7, wherein the thermal management device adjusts the temperature within the housing by at least one of forced fluid convection and forced air convection.

11. The device of claim 7, wherein the temperature sensor transmits data to a controller located remotely from the device.

12. The device of claim 7, further comprising a heat sink positioned in the housing, wherein the thermal management device adjusts the temperature within the housing by removing heat from the heat sink by at least one of thermo-electric cooling, forced fluid convection and forced air convection.

13. A system for monitoring a sample, the system comprising:

a laser for generating a light wave;

a transmitter coupled to the laser by a fiber optic cable for receiving the light wave, the transmitter generating output radiation in the frequency range of 10 GHz to 100 THz, wherein the output radiation is directed to the sample;

a radiation detector for receiving and processing radiation emanating from said sample and a time gating pulse for providing a time gated detector output;

a housing having the transmitter and the radiation detector therein;

wherein at least one of the transmitter and the radiation detector has a thermal management device and a temperature sensor that are both in thermal communication with the housing, and a controller for actuating or otherwise adjusting the thermal management device, wherein the temperature sensor measures a temperature associated with the housing, and wherein the thermal management device adjusts the temperature associated with the housing based on the measured temperature.

14. The system of claim 13, wherein the thermal management device is a thermo-electric device, and the thermo-electric device has a first portion disposed inside of the housing and a second portion disposed outside of the housing.

15. The system of claim 13, wherein the thermal management device adjusts the temperature associated with the housing by at least one of forced fluid convection and forced air convection.

16. The system of claim 13, wherein the controller is located remotely from the transmitter and the radiation detector.

17. The system of claim 13, wherein the thermal management device has a heat sink positioned in the housing, and wherein heat is removed from the heat sink by at least one of thermo-electric cooling, forced fluid convection and forced air convection.

18. The system of claim 13, wherein information associated with at least one of the measured temperature associated with the housing and the adjustment of the temperature associated with the housing is presented by the controller.

19. The system of claim 13, further comprising a purging device in fluid communication with the sample or process, wherein the purging device applies an inert gas to a path of the radiation in proximity to the sample or process.

20. The system of claim 13, wherein the thermal management device is a thermionic device.

* * * * *

UNITED STATES PATENT AND TRADEMARK OFFICE
CERTIFICATE OF CORRECTION

PATENT NO. : 7,795,582 B2  
APPLICATION NO. : 11/875415  
DATED : September 14, 2010  
INVENTOR(S) : David R. Jez and Frank M. Haran Page 1 of 1

It is certified that error appears in the above-identified patent and that said Letters Patent is hereby corrected as shown below:

Title page, item [73]

Assignee should be changed to:

--Honeywell ASCA Inc., 3333 Unity Drive, Mississauga ON, L5L 3S6, Canada--

Signed and Sealed this  
Twenty-fifth Day of January, 2011

David J. Kappos  
*Director of the United States Patent and Trademark Office*